(12) United States Patent
Kynast et al.

(10) Patent No.: US 6,416,520 B1
(45) Date of Patent: Jul. 9, 2002

(54) MICRODRIVE FOR PROBES

(75) Inventors: Lutz T. Kynast, Suwanee, GA (US); William Rittman, Lynnfield, MA (US); James P. O'Connor, Bulerica, MA (US); Michael Cundari, Hingham, MA (US); Eric Cosman, Belmont, MA (US)

(73) Assignee: Sherwood Services AG, Shaffhausen (CH)

( * ) Notice: Subject to any disclaimer, the term of this patent is extended or adjusted under 35 U.S.C. 154(b) by 0 days.

(21) Appl. No.: 09/552,779

(22) Filed: Apr. 20, 2000

Related U.S. Application Data

(60) Provisional application No. 60/130,867, filed on Apr. 23, 1999.

(51) Int. Cl.[7] .............................................. A61B 19/00
(52) U.S. Cl. ..................................................... 606/130
(58) Field of Search ............................ 606/130, 53–59, 606/129, 131; 600/429, 426, 417

(56) References Cited

U.S. PATENT DOCUMENTS

| 3,817,249 A | 6/1974 | Nicholson | |
| 5,154,723 A | * 10/1992 | Kubota et al. | 606/130 |
| 5,413,103 A | 5/1995 | Eckhorn | |
| 5,643,286 A | 7/1997 | Warner et al. | |
| 5,817,106 A | 10/1998 | Real | |
| 5,871,487 A | 2/1999 | Warner et al. | |
| 6,117,143 A | * 9/2000 | Hynes et al. | 606/130 |

FOREIGN PATENT DOCUMENTS

| EP | 0 571 827 A1 | 12/1993 |
| WO | WO 96/00044 | 1/1996 |
| WO | WO 98/51229 | 11/1998 |

* cited by examiner

*Primary Examiner*—Kevin Truong

(57) ABSTRACT

A probe is connected to a probe carrier that is positioned with respect to the body of a patient. The probe is moved into or out of the body incrementally by means of a driver mechanism and flexible coupler. The flexible coupler in one embodiment comprises a flexible sheath with a flexible driver shaft that can be passed within the flexible sheath and can be rotated or pushed forward and backward with respect to the sheath by a driver element thereby causing translational movement of probe. Several forms of probes, flexible coupling elements, and driver apparatus as well as methods of applications accommodate specific objectives.

17 Claims, 2 Drawing Sheets

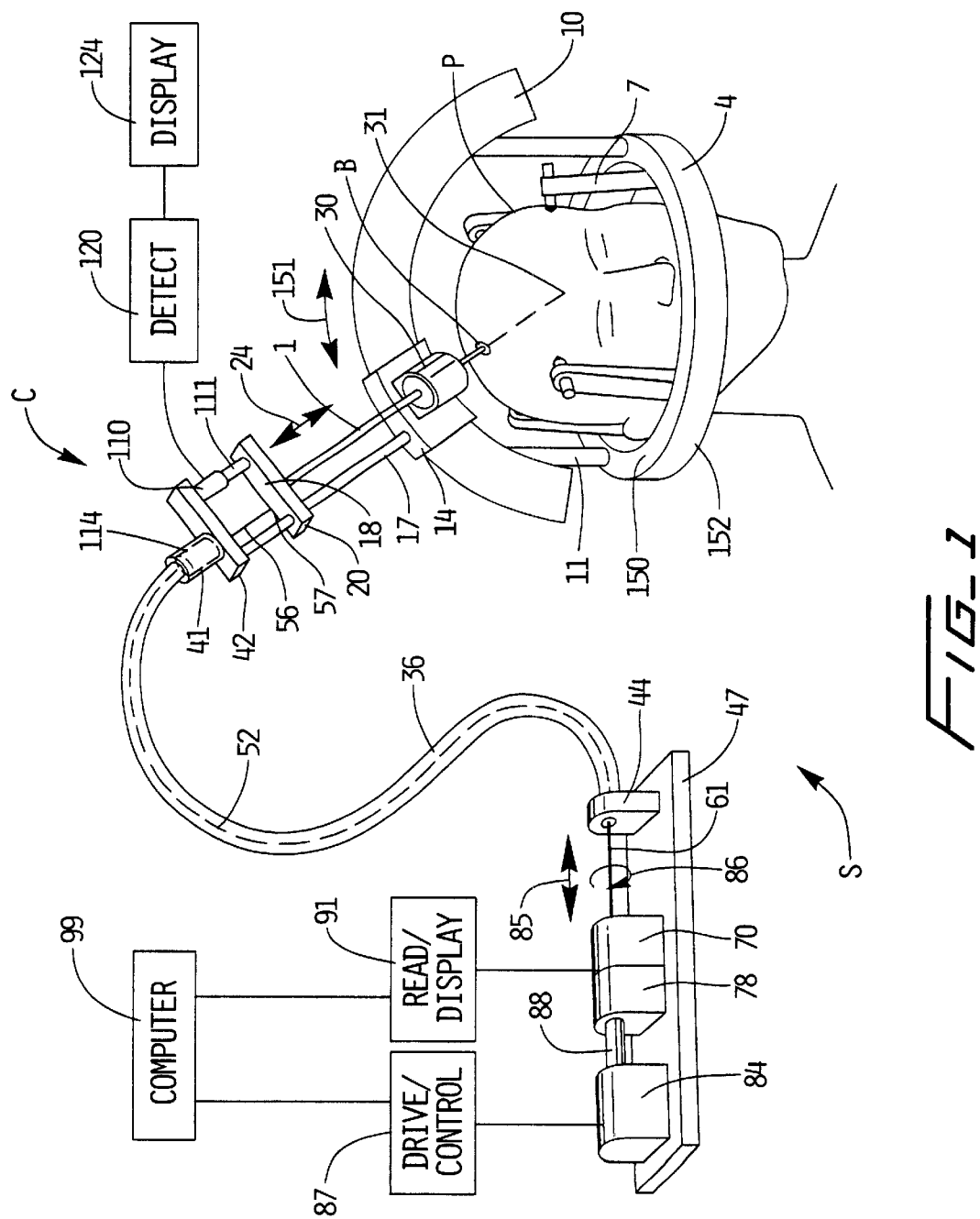
FIG_1

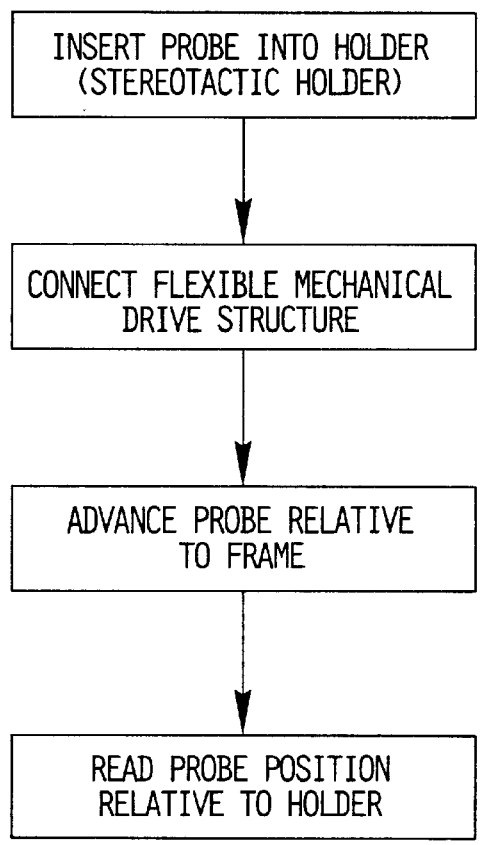
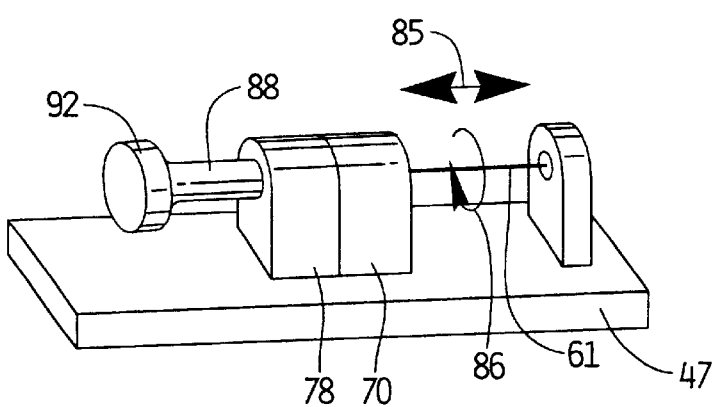

MICRODRIVE FOR PROBES

This application claims benefit of provisional application No. 60/130,867 filed Apr. 23, 1999.

FIELD OF THE INVENTION

This invention relates generally to advances in medical systems and procedures for prolonging or improving human life. More particularly, this invention relates to an improved method and system for advancing a probe or an electrode into the human body in finely graded steps while detecting the position of the probe advancement.

BACKGROUND OF THE INVENTION

In the field of neurosurgical stereotaxy, electrodes and probes of various kinds may be advanced into the brain of a patient. In the case of deep brain stimulation (DBS) or radiofrequency (RF) lesion making, microelectrodes are typically advanced from a stereotactic frame into the brain in very small steps, sometimes of micron incrementation. These microelectrodes typically have tips with lengths of several microns to several hundred microns. In some applications recordings of electrical activity of brain cells deep in the brain are recorded by electrical signal monitoring from the microelectrode as it is incrementally advanced into the brain.

Microdrives for such brain probes may include mechanical sliding devices and mechanical screw devices that are attached to the carrier of the stereotactic frame. These devices typically are cooperatively connected to the probe so that advancement of the probe into the patient's brain, for example, can be done while visually reading a mechanical scale or digital readout. In some instances, the operation of these devices involves turning a mechanical screw or rack-and-pinion to advance the position of the electrode mechanically.

By reference, the stereotactc frames of Radionics, Inc., Elekta AB, and the TrentWells, Inc. stereotactic systems illustrate the use of stereotactic frames and recording probes.

The capability to advance an electrode in fine steps, on the order of several tens of microns (micrometers) to several hundred microns presents certain technical problems. Mechanical motions of the electrode or the advancing device can disturb the highly sensitive electrical recording measurements of electrical brain activity. For similar reasons, it may be advantageous to electrically decouple moving device from the electrode. Hydraulic microdrives have been used to provide fine verniated movements. The hydraulic microdrives comprise a flexible hydraulic tubing that advances an incompressible fluid within the tubing to drive a piston which is coupled to the electrode near the stereotactic frame. By reference, the electrode microdrive of the TrentWells, Inc. company (Los Angeles, Calif.) is an example of a hydraulically advanced microdrive for stereotactic probes.

Difficulties with hydraulic microdrives include fluid leaks and problems with sterilization. For example, steam autoclave sterilization disrupts the hydraulic fluids that are contained in the enclosed, flexible tubing. Furthermore, the ability to monitor the position of the electrode at the position of the probe carrier on the stereotactic frame has been difficult. By reference, the hydraulic probe microdrive of the TrentWells, Inc. company does not provide detection means at the probe end near the stereotactic frame end of the hydraulic tubing. Rather, this microdrive only provides deflection means at the side near the hydraulic piston, which is remote from the stereotactic frame.

It is important for a surgeon to know the actual position of the probe at the stereotactic frame for quantitative evaluation of the position of the probe. However, mechanical screw type, rack-and-pinion, or millimeter slide type probe carriers on the stereotactic frame prove relatively ineffective in achieving fine distance verniations (e.g. on the order of tens of microns) without creating electrical disturbance of the brain recordings.

Accordingly, an effective technique and system for stereotactic probe advancement, especially when fine advanced movements are required and electrical recording is required, is desirable for purposes of stereotactic probe placement. Particularly in the surgical setting, a need exists for a microdrive for probes which does not rely on fluid coupling and which can be readily cleaned and sterilized.

SUMMARY OF THE INVENTION

The present invention is directed to a mechanical microdrive system and method for smooth and reliable advancement of a probe with respect to a probe carrier. The present invention is different from any of the systems discussed in the Background section. Advantages of the present system and method reside in their simplicity, mechanical stability, ability to be sterilized and cleaned for surgical use, ruggedness and reliability, and clinical effectiveness.

In one embodiment, the mechanical microdrive includes flexible tubing that contains a flexible but longitudinally rigid push cable (push rod). The tubing is connected on its distal end to a stereotacic carrier attached to a stereotactic frame. The flexible push rod is attached independently to a microelectrode holder that advances the microelectrode stereotactically into the patient's body. On the proximal end, the flexible tubing is attached to a platform, and the flexible push rod is advanced within the tubing by an advancing mechanism. The advancing mechanism can have very fine longitudinal position gradations and have readout and display of its position. It is driven either manually or by a motor. At the stereotactic frame, the relative position of the probe is measured by a detecting system to give a position of the advancement of the probe into the patient's body. Electrical signals from the driving mechanism and the probe position mechanism can be sent to a computer or other display to control the process.

One embodiment of the mechanical flexible advancement device utilizes a longitudinal advancement of the push rod within the device as provided by a rotatable internal drive rod which enables a screw advancement at the proximal end by the stereotactic device.

The present technique avoids many of the difficulties associated with a hydraulic microdrive. For example, since a hydraulic transmission fluid is not used within the system, difficulties of autoclaving and unwanted leaks are avoided. In addition, a system conducted according to the present invention may be cleaned and sterilized by using autoclave and other means, thus simplifying the surgical preparation. Such a system has further advances of simplicity and robustness. It does not need to be filled with a hydraulic fluid and does not have problems associated with bubble formation within the hydraulic tube, as does the hydraulic microdrive described in the Background section.

These features and advantages, as well as others of the present method and system, will become apparent in the detailed description that follows.

BRIEF DESCRIPTION OF THE DRAWINGS

In the drawings which constitute a part of the specification, embodiments exhibiting various forms and features hereof are set forth, specifically:

FIG. 1 is a schematic diagram showing one embodiment of a probe being advanced relative to a stereotactic holder by a flexible mechanical probe microdrive in accordance with the present invention.

FIG. 2 shows a flow chart of a process that may be performed by a system in accordance with the present invention.

FIG. 3 illustrates an alternative embodiment utilizing a manual device for advancing the flexible coupler.

DETAILED DESCRIPTION OF THE INVENTION

Referring initially to FIG. 1, in a system S in accordance with the present invention, a probe 1 is advanced into the body of a patient P. The patient is fixed in a stereotatiic frame which comprises a headring structure 4 that is secured firmly to the patient's head by posts such as 7. The headring platform includes support structures 11 that support a stereotactic arc system 10 which may be slidable engaged with a probe carrier structure C. The probe carrier structure C includes a probe carrier 14 that has a probe post 17 that supports a probe drive block 20. The probe drive block 20 moves in and out relative to the stereotactic frame as indicated by the arrow 24. The probe drive block 20 is attached at connection 18 to the electrode 1, and advances the electrode into or out of the brain in the directions indicated by arrow 24. The probe 1 is guided through a guide block 30 for directional stability. By reference, the CRW stereotactic arc system of Radionics, Inc. (Burlington, Mass.) includes examples of guide carriers for probes.

Also shown in FIG. 1 is a flexible mechanical probe drive tube 36, which connects at one end to a coupler 41 affixed to the stereotactic probe carrier structure C. On the other end, the tube 36 is connected to a block 44 attached to a drive apparatus base 47. Inside the tube 36 is a mechanical and flexible internal drive structure 52, indicated by the dashed line in FIG. 1. The internal drive structure 52 (e.g., a cable) emanates from the tubing 36 at its distal end, as illustrated by element 56, and may connect by connection 57 to the electrode or probe drive block 20.

On the proximal end, the internal drive structure 52 emanates from the tubing 36 as illustrated by drive or driver element 61 (e.g., a push rod) 44 and connects to a drive device 70. The drive device 70 may, for example, be a transmission or hydraulic moving device or a geared vernier translator. Examples of vernier translators are the fine movements in a vernier caliper used in mechanical measurements in machine shops (for example, supplied by the Starrett Company, Athol, Mass.).

Also shown in FIG. 1 is a movement encoder or detection device 78 which can provide mechanical or electrical output indicative of the position of the drive device 70; and henceforth, the position of element 61. The drive device 70 (e.g., translator) can be driven by driver 84, which can be a motor or a manual device for turning a shaft 88 or otherwise actuating the vernier translation device 70. FIG. 3 illustrates a manual device having a rotation knob 92.

A drive device 70 can be controlled or powered by a drive control element 87. The drive device 70 also may incorporate various display elements 91 to indicate the position of the drive element, and therefore of the push rod 61. Electronic output or control signals of elements 87 and 91 can communicate with computer 99 for automation of the system or other control aspects. Computer 99 may have stereotactic planning information in it based on CT, MR, or other image data. The computer 99 may provide an electronic readout from a microelectrode such as electrode 1 that has its tip positioned deep within the brain (e.g. position 31). This readout information can be correlated with the position of the encoder 78 or an encoder on the probe carrier structure C as described below.

The drive shaft (e.g., elements 61, 52, and 56) may, for example, be a longitudinal push-pull type or rotational-type wire or structure. The indication of these motions are shown schematically by the translation arrow 85 and the rotation direction 86, respectively. The drive shaft can move, for example, longitudinally with the sheath or carrier 36 or rotate within it. For example, in the first case, the drive device 70 causes linear movement of element 61. This movement, in turn, causes drive structure 52 to move linearly within the tube 36; the ends of tube 36 being fixed to block 44 and coupling 41. The movement of drive structure 52, in turn, causes element 56 to move in a linear fashion, thereby causing drive block 20 to move as indicated by arrow 24. It should be appreciated that, in general, the drive shaft components 61, 52 and 56 are constructed of material of sufficient rigidity to cause predictable linear movement of drive block 20 in response to a given linear translation by drive device 70.

In the case of a rotational drive shaft, the shaft may connect to a rotational transmission within coupling 41, which for example, may include a threaded not 114 such that rotation of the shaft and the nut corresponds to a pushing or pulling motion on the electrode or probe 1, as indicated by arrow 24. Thus, the coupling 41 translates the rotational movement of the drive structure 52 into linear movement of element 56. It should be appreciated that, in general, the drive shaft components 61, 52 and 56 are constructed of materials of sufficient rigidity to cause predicable linear movement of drive block 20 for a given angle of rotation of drive device 70. For example, the rotating components (element 61 and drive structure 52) typically would be sufficiently rigid with respect to the rotational forces to which they are subject. Element 56 would be sufficiently rigid with respect to the linear forces to which it is subjected.

Note that, depending upon the coupling type, the element 56 also may rotate. In this case, the connection 57 would include a rotating member that connects to the rotating element 56.

Also shown in FIG. 1, in accordance with the present invention, is an apparatus to detect the actual movement of the electrode 1 with respect to its probe carrier 14 and therefore with respect to the stereotactic frame 10 and the patient's body P. For example, a probe carrier plate 42 can have connected to it a linear translation detection device 110, which detects the movement of the drive block 20 with respect to the probe carrier plate 42. As the drive block 20 moves in and out, as illustrated by the arrow 24, the shaft element 111, which is connected to the probe 1 by drive block 20, moves with respect to the base of the detection device 110. This combination of 110 and 111 elements could, for example, be a linear translation detection/measuring device that is used for detection of linear motions. By reference, see, for example, descriptions of Linear Variable Differential Transformer (LVDT) devices illustrated by the products of Lucas/Schaevitz Company, USA. As the probe 1 moves in and out of the patient's body, as driven by drive shaft 56, the actual position of the probe 1 with respect to the stereotactic frame is therefore detected by the translation detection elements 110 and 111 and by sensing or detecting apparatus 120. The apparatus 120 may, for example, translate induction, capacitor, resistance, or other electrical parameters associated with or provided by the detection device 110 into a measurement signal (e.g., representing millimeters or inches) corresponding to the advancement position of probe 1. The position of the probe also may be visually represented on display element 124, which may be part of a computer system, a CRT, a flat screen LCD, or other analog or digital display. The display may be cooperatively connected to computer 99 so that a comprehensive measurement and control system is integrated between the drive and measurement elements as described above.

In accordance with the present invention, various probes or electrodes may be used in the system shown in FIG. 1. For example, the probe 1 may be a microrecording electrode having a conductive electrode tip exposure in the range of 1 to several microns. The probe 1 may be a semi-microelectrode where the exposed recording and stimulating tip has larger dimensions (e.g, on the order of tens to hundreds of microns). The probe 1 may be a macrostimulation, lesioning, or recording electrode having a tip adapted to do gross stimulation, recording, or heat lesioning. The probe 1 also may be part of a deep brain stimulation system. By reference, recording, stimulating, lesioning, and deep brain stimulating electrodes are represented in the product line of Radionics, Inc., Burlington, Mass., or Medtronic, Inc., Minneapolis, Minn.

Referring to FIG. 2, a process is shown in accordance with the present invention in which a probe is advanced into the patient's body. The probe may be held and stabilized in a stereotactc device, as shown in FIG. 1, or some other type of actuator such as a robot, image-guided system, or alternative types of stereotactic apparatus. The insertion of the probe into the holder and its attachment is illustrated by step 1 in FIG. 2. After insertion of the probe into the stereotactic holder, connection can be made via the flexible mechanical drive structure (step 137). The driver on the distal end can be connected to adaptions (e.g., 41) that allow advancement of the probe into the patient's body. On the proximal end, the flexible drive structure may be connected to the drive mechanism with verniated readout on the driver end (e.g., 70, 78). After appropriate registration of the probe relative to the stereotactic frame, the probe may be advanced incrementally into the patient's body (step 140). The advancement may be accompanied by detection and readout of the probe position and/or the driver position, as described in the embodiment of FIG. 1. That information can be connected to computer, control, and/or display apparatus to control monitor, and indicate the probe position relative to the stereotactic frame and/or the patient's body (step 144).

Other steps may follow the steps of FIG. 2 and may include, in the case of neurosurgery, recording, stimulating, or producing a radiofrequency lesion and displaying parameters associated with these functions on a display or computer system. Correlation of the displays of these parameters can be made with scan data or other representations of anatomy associated with the patient's body or atlases that are registered with the patient's body.

The system and method of the present invention has the advantage that a flexible mechanical drive coupling provides versatility of position of the proximal drive device relative to the probe and stereotactic frame. When delicate recording, stimulation, or lesioning is required from the probe, vibration isolation of the drive device through a flexible mechanical driver (e.g., driver tube 36, as illustrated in FIG. 1, advantageously reduces electrical noise and mechanical vibration of the probe. Another advantage of the invention is that the flexible mechanical drive system, does not have the handling and sterilizing problems of a hydraulic probe microdrive, as described in the Background section. A tubing filled with incompressible fluid to drive the probe is subject to bubble lock, leaks, contamination and is difficult to autoclave and sterilize and clean. The present invention has the advantage that it is simple, robust, easy to clean and handle, poses no leak contamination risks, and can be sterilized. Another advantage of the present invention is that the mechanical driver can be electrically isolated from the probe. The flexible tubing 36 and drive shaft 52, as shown in FIG. 1, may be made of electrical insulative material or have insulative couplings at its proximal or distal end to isolate the drive device from the probe carrier. Moreover, the driver (e.g., motor) can also be placed at a somewhat remote location, for example several inches to several feet away from the probe, to eliminate electrical noise and capacitive or inductive noise. As an example, the drive sheath 36 (tubing) in FIG. 1 can be made from a Teflon, PVC, polyurethane, or braided plastic and metal structure which is fully insulated and flexible. The inner drive element 52 can be made from a metal wire coated by an insulative and low friction material such as Teflon. At the proximal end in the bushing 44 or the distal end in the busing 41, the drive element can be electrically insulated from the drive device 47 or from the probe carrier 42.

To enable positioning of probe 1 to virtually any location in the patient's head, the probe carrier 14 may be movable with respect to the headring structure 4. For example, probe carrier 14 may be slidably attached to arc system IO so that the probe carrier 14 moves in the direction indicated by arrow 151. The arc system 10 may be movable with respect to the headring structure 4. For example, member 150 (connected to structure 11) may move with respect to member 152 (connected to posts 7). Arc system 10 also could be adapted to linearly move relative to headring structure 4, for example, as is known in the art.

Various devices for measuring the probe position corresponding to element 110 can be devised. LVDT, capacitive distance measurements, inductive devices, vernier calipers, digital LCD readouts, rheostat or resistive displacement devices, or other means can be used to provide accurate position and displacement, both absolute and incremental measurements. In view of these considerations, as would be apparent by persons skilled in the art, implementations and systems should be considered broadly and with reference to the claims set for below:

What is claimed is:

1. A system for driving a probe into the body of a patient, comprising:

a probe carrier adapted to be positioned with respect to the body of a patient and to guide a probe which is to be advanced into the body of the patient;

a driver apparatus comprising a base and a driver element which moves with respect to the base;

a flexible coupler connecting said base to said probe for connecting the probe and the driver element so that movements of said driver element with respect to said base will cause movements of said probe with respect to said probe carrier and cause advancement or retraction of said probe into the body of the patient.

2. The system of claim 1, wherein the flexible coupler comprises a flexible sheath and a drive shaft that can be driven with respect to the flexible sheath, the drive shaft connected at a distal end to the probe and at a proximal end to the driver element.

3. The system of claim 2 wherein said drive shaft comprises a flexible metal element that passes within said flexible sheath, and said driver element pushes said drive shaft forward inside said flexible sheath, thereby causing said probe to move forward with respect to said probe carrier and with respect to the body of the patient.

4. The system of claim 2 wherein said drive shaft comprises a flexible metal element and said driver element rotates said drive shaft within said flexible sheath, and said probe carrier further comprises a rotation-to-translation converter that is cooperatively connected to said drive shaft so that when said drive shaft is rotated with respect to said flexible sheath, said rotation-to-translation converter translates the rotation of said driver shaft translational rotational movement of said driver shaft into a forward or retraction movement of said probe with respect to said body of the patient.

5. The system of claim 4 wherein said rotation-to-translation converter comprises a screw element to convert rotations of said driver shaft to translations of said probe into or out of said body of the patient.

6. The system of claim 1 and further including a movement detector connected to said probe carrier and to said probe to provide output data on the position of said probe with respect to said probe carrier.

7. A system for driving a probe into the body of a patient comprising:

a probe carrier adapted to be positioned with respect to the body of a patient and to guide a probe which is to be advanced into the body of a patient;

a driver apparatus remote from the probe and having a driver element;

a connector connecting the remote driver apparatus and the probe carrier to mechanically advance and retract the probe so that movement of the driver element will cause movements of the probe with respect to the probe carrier and with respect to the body of the patient.

8. The system of claim 7, further including a movement detector connected to said probe carrier and to said probe to provide output data on the position of said probe with respect to said probe carrier.

9. The system of claim 8, further comprising a detection device for indicating the position of the driver element.

10. The system of claim 8, wherein the connector comprises a flexible drive shaft.

11. The system of claim 10, wherein the flexible drive shaft is at least partially contained within a sheath.

12. The system of claim 10, further comprising a manual control knob for advancing the flexible drive shaft.

13. A system for driving a probe into the body of a patient comprising:

a probe carrier adapted to be positioned with respect to the body of a patient and to guide a probe which is to be advanced into the body of a patient;

a driver apparatus remote from the probe and having a driver element, the driver element actuable to advance and retract the probe with respect to the probe carrier and patient; and a movement detector positioned adjacent the probe carrier to detect the position of the probe.

14. The system of claim 13, wherein the movement detector is connected to a probe carrier attachment and includes a linear translation detection device.

15. The system of claim 14, wherein the probe carrier attachment comprises a probe carrier plate having a shaft element extending therefrom, the shaft element being connected to the probe.

16. The system of claim 15, further comprising a driver block connecting the shaft element to the probe.

17. The system of claim 13, further comprising a display element connected to the movement detector to visually represent the position of the probe.

* * * * *

UNITED STATES PATENT AND TRADEMARK OFFICE
CERTIFICATE OF CORRECTION

PATENT NO.   : 6,416,520 B1
DATED        : July 9, 2002
INVENTOR(S)  : Lutz et al.

It is certified that error appears in the above-identified patent and that said Letters Patent is hereby corrected as shown below:

<u>Title page,</u>
Item [75], Inventors, "James P. O'Connor, Bulerica, MA" should read -- James P. O'Connor, Billerica, MA --

Signed and Sealed this

Twenty-eighth Day of September, 2004

JON W. DUDAS
*Director of the United States Patent and Trademark Office*